United States Patent [19]

Ochi et al.

[11] Patent Number: 5,563,258

[45] Date of Patent: Oct. 8, 1996

[54] SUCRALFATE AQUEOUS SUSPENSION AND ITS METHOD OF PREPARATION

[75] Inventors: Kiyoshige Ochi; Kazuo Sasahara; Mituo Shiratori; Sakae Takaku, all of Saitama-ken, Japan

[73] Assignee: Chugai Seiyaku Kabushiki Kaisha, Tokyo, Japan

[21] Appl. No.: 429,512

[22] Filed: Apr. 26, 1995

Related U.S. Application Data

[63] Continuation of Ser. No. 971,980, filed as PCT/JP91/01114, Aug. 22, 1991, abandoned.

[30] Foreign Application Priority Data

| Aug. 31, 1990 | [JP] | Japan | 2-232305 |
| Sep. 6, 1990 | [JP] | Japan | 2-236161 |
| Nov. 26, 1990 | [JP] | Japan | 2-321449 |
| Apr. 15, 1991 | [JP] | Japan | 3-082526 |

[51] Int. Cl.$^6$ .............. C07H 11/00; C07H 1/00; A61K 31/715

[52] U.S. Cl. .......... 536/118; 536/121; 536/122; 536/124

[58] Field of Search .............. 536/118, 122, 536/124, 121; 514/53

[56] References Cited

U.S. PATENT DOCUMENTS

| 3,432,489 | 3/1969 | Nitta et al. | 536/118 |
| 4,650,888 | 3/1987 | Ochi et al. | 556/177 |
| 4,668,665 | 5/1987 | Ishihara et al. | 514/53 |
| 4,885,281 | 12/1989 | Hanstein et al. | 514/53 |
| 4,990,610 | 2/1991 | Lazaridis et al. | 536/118 |
| 5,084,446 | 1/1992 | Baldoni et al. | 514/53 |

FOREIGN PATENT DOCUMENTS

| 1500571 | 11/1966 | France . |
| 107934 | 5/1988 | Japan . |
| 64-45312 | 2/1989 | Japan . |
| 8905645 | 6/1989 | WIPO . |
| 9002133 | 3/1990 | WIPO . |
| 9005260 | 5/1990 | WIPO . |

*Primary Examiner*—Douglas W. Robinson
*Assistant Examiner*—Everett White
*Attorney, Agent, or Firm*—Browdy and Neimark

[57] ABSTRACT

This specification discloses a production process for an sucralfate aqueous suspension stock, the process being characterized by direct dispersement of an sucralfate aqueous stock for sucralfate preparations, which contains sucralfate particles with an average particle size of no more than 50 μm in a concentration of 1–2 g/ml, in water or other aqueous medium without drying the synthesized sucralfate wet powder, followed by milling of the sucralfate particles to an average particle size of no more than 50 μm. When the sucralfate aqueous suspension stock obtained directly from wet powder in accordance with this method is compared to the conventional suspension obtained from dry powder, equivalency of both stocks are obtained in terms of both properties and pharmacological activities. In comparison to the conventional process using dry powder, this wet milling method of production is economically and operationally superior and environmental pollution arising from the conventional process can be prevented.

6 Claims, 4 Drawing Sheets

5,563,258

SUCRALFATE AQUEOUS SUSPENSION AND ITS METHOD OF PREPARATION

This application is a continuation of application Ser. No. 07/971,980, filed Feb. 19, 1993, now abandoned.

FIELD OF THE INVENTION

This invention relates to aqueous suspension stock for use in production of preparations of basic aluminum salt of sucrose sulfate (sucralfate) and its method of production.

BACKGROUND OF THE INVENTION

Sucralfate is used as a therapeutic agent in the treatment of gastritis, and gastric and duodenal ulcers.

The selective adhesion of sucralfate on the ulcer or area of inflammation is crucial for the manifestation of sucralfate's therapeutic effects. Sucralfate's physiological features are as follows: sucralfate's particles are non-selectively adhered on the tissue protein; sucralfate-adheres to the injured area upon contact with the gastric juice, which increases the viscosity of the sucralfate; and through the manifestation of a combined action which binds the sucralfate to the pepsin dispersed in the stomach and consequently inactivates the pepsin, the sucralfate improves the organism's recovery mechanism and promotes the functioning of the organism's defense system resulting in cure of the ulcer or inflammation.

As described in Japanese Patent Publication Nos. 44-11673 and 44-16037, sucralfate is obtained by reaction between the salts of sucrose sulfate and basic aluminum chloride, and the resulting wet powder is dispersed, and then heat drying (spray drying). The resulting dry powder is used as the bulk material when producing solid preparations due to ease of production.

Taking into account sucralfate's insolubility in water and its mechanism of adhesion on protein, it is important to mill the sucralfate as finely as possible in order to increase its surface area.

Conventionally, the sucralfate aqueous suspension has been prepared by mechanically milling sucralfate dry powder, obtained from wet powder by heat-drying, and then recombining the dry powder with water and then preparing the final product. This method of production is not considered technologically advanced due to certain inherent flaws; specifically, (1) this method of production, which consists of a process of drying, milling, and then resuspending the dry powder in water, is operationally defective and entails high costs, (2) there is considerable variation in particle size due to milling of the powder in a dried form, (3) there are pollution problems which arise in the workplace due to fine powder escaping during milling, and (4) pollution is likely to occur due to escaping particles of milled sucralfate powder when filling and sealing containers or when adjusting the production process.

Moreover, since the conventional method requires that once reaction with basic aluminum chloride is complete the resulting sucralfate wet powder be separated by centrifugal manipulation and then dried, it was not possible to design an industrially successive or continuous production process or to plan for efficiency in mass production.

DISCLOSURE OF THE INVENTION

By employing the method(s) described in Japanese Patent Publication Nos. 44-1673 and 44-16037, for example, namely causing a reaction between the salts of sucrose sulfate and basic aluminum chloride (e.g., aluminum hydroxychloride, polyaluminum chloride), the sucralfate pertaining to this invention is obtainable.

The wet sucralfate is then washed with water, suspended in either water or other aqueous medium, and subjected to milling process. In order to formulate a sucralfate suspension stock of the desired concentration, the volume of the stock can be adjusted by adding or removing the appropriate amount of medium. If necessary, however, the wet sucralfate powder before centrifugal separation or other such method can be used, as suspended in water or other aqueous medium and subjected to milling. The volume of water or other aqueous medium can then be increased in order to obtain the desired concentration in the sucralfate suspension stock.

In an embodiment of this invention, the aqueous suspension stock for production of sucralfate preparations is obtained by directly milling the separated wet powder, omitting the drying step after reaction between sodium sucrose sulfate and basic aluminum chloride and followed by washing the resulting sucralfate in water. The washing procedure is needed to remove the unreacted material, as well as the comparatively large quantity of chlorine ions present as a result of the reaction, which remains in the reaction mixture during sucralfate production. In this invention, the reaction by product as above is eliminated through the repeated process of allowing the mixture to precipitate, exchanging the supernatant with water, agitating the mixture, and again allowing the mixture to precipitate; finally, the mixture is centrifuged and the sucralfate wet powder results. After dispersing and milling this wet sucralfate in water or other aqueous medium, sucralfate suspension stock is obtained.

In another embodiment of this invention, the desired sucralfate aqueous suspension stock is obtained by milling the dispersed sucralfate without prior centrifugation, that is, the dispersed sucralfate in water is obtained from the reaction mixture through repeated process as above. With this method, it is possible to reduce the chlorine ion which arises during the reaction and reduce the number of washing cycles by using a basic aluminum chloride substance, such as basic polyaluminum chloride of higher basicity degree in the reaction. Additionally, by deleting the centrifuging step, this method simplifies the suspension stock production process, thereby making the process suitable for mass production and reducing the amount of wastes.

In regard to the concentration of the sucralfate suspension stock produced by this invention, the desired concentration can be set by adjusting the amount of water or other aqueous medium present at the time of milling. A sucralfate concentration of 1–2 g/ml and if possible in the range of 1.1–1.5 g/ml is considered preferable. The closer the concentration is to 1.2 g/ml, the more desirable. In particular, the average particle is preferable under 50 μm. If the sucralfate concentration is set at 1.1–1.5 g/ml, an even, stable sucralfate suspension stock, difficult to separate into water and slurry components, is obtainable.

Provided the milling apparatus used to mill the sucralfate forms particles under 50 μm, there are no particular requirements for the type of machine used. The time required to micronize the particles depends on the capabilities of the apparatus, but normally it is advisable that the micronization process is repeated for 3–30 minutes, or if possible 5–20 minutes, at room temperature or below temperature with cool water (10°–25° C.) until the desired particle size is attained.

It is possible to add certain preservatives, such as benzoic acids, or p-hydroxy benzoic acid esters, and chlorobutanol, to the aqueous medium described in this invention in order to prevent the spread of microbes and other such organisms. This sort of preservative does not affect the characteristics of the sucralfate itself and allows, for example, transport of The substance from production site to preparation produced site and long-term storage of the suspension stock in containers. Additionally, it is possible to heat sterilize the sucralfate suspension stock either in addition to or instead of adding a preservative. Heat treatment is normally performed after production of the liquid bulk substance, before long-term storage or movement to a different preparation or production facility, for example. It is preferable to perform sterilization at about 95°–100° C. for approximately 10–30 minutes.

The sucralfate aqueous suspension stock obtained from this invention is used as stock for sucralfate suspension preparations either as is or in a diluted form depending on the concentration; it can also be used as the stock for producing preparations such as an aqueous cream or a poultice.

Figure 1:
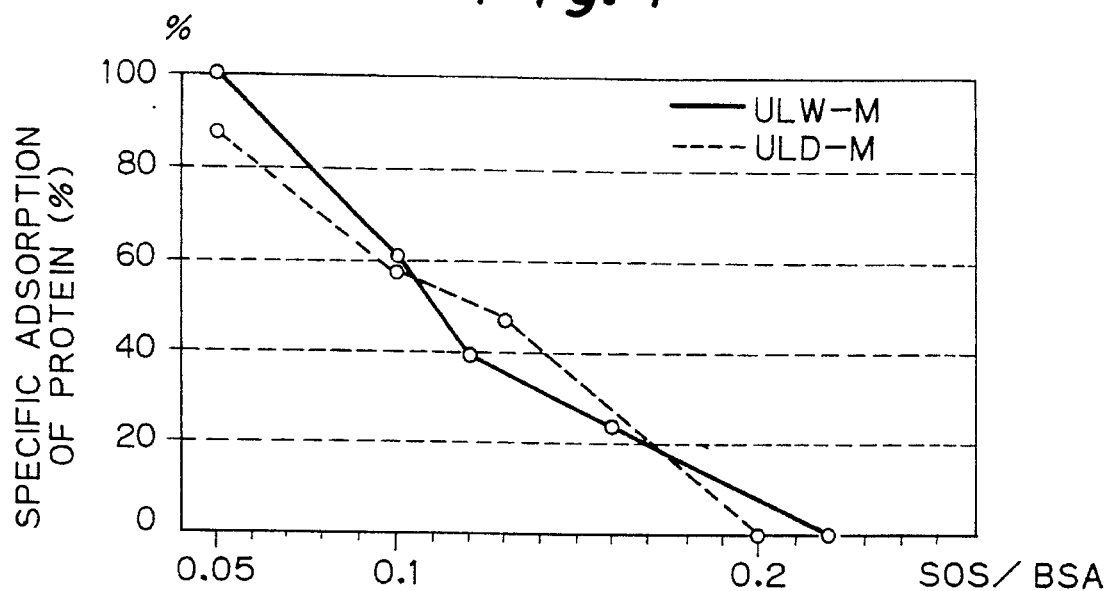
FIG. 1 is a graph comparing the protein binding properties of sucralfate aqueous suspension stock produced by the wet method of this invention (ULW-M) and suspension stock produced by the conventional dry method (ULD-M).

The following are reference examples, cases, and experimental examples, intended to further clarify this invention. The breadth of this invention is not, however, limited to these examples.

Reference Example 1

Method of producing wet sucralfate

When 10 g of sodium sucrose sulfate (sulfur content of 11.74%) was dissolved in 100 ml of water, and gradually combined with a mixture of 6 g of aluminum dihydroxy chloride dissolved in 100 ml of water, a white-colored o precipitation slowly became visible. Next, the pH was adjusted to 4.5–5.0 by adding 1N sodium hydroxide, after which the solution was agitated for about 30 minutes at room temperature, and the white-colored precipitation was filtered. After washing the precipitation several times with water and removing the unreacted sucrose sulfate, 17.2 g of wet powder was obtained. The powder had an aluminum content of 14.2% and a sulfur content of 8.61%.

Reference Example 2

Preparation of aqueous suspension stock using dry sucralfate powder (conventional method)

When 800 ml of water was added to 380 g of sucralfate wet powder obtained by the method described in Reference Example 1 and agitated at high speed (3000–4000 rpm), sucralfate slurry was obtained. The slurry was then sprayed under pressure from the upper section of a spray dry apparatus, and simultaneously treated with blowing hot air, 155°–220° C., also from the same upper section, thereby removing the moisture in the slurry. The sucralfate dry powder was then removed from the lower section of the apparatus and subsequently micronized using an impact pulverizer. By suspending the resulting 1 g of milled, micronized sucralfate dry powder in 4 ml of water, about 5 ml of sucralfate aqueous suspension was produced.

Reference Example 3

Production of basic aluminum chloride

Ten grams of aluminum chloride hexahydrate were dissolved in 45 ml of distilled water, after which 3.35 g of granular metallic aluminum was added. The mixture was then heated by steam bath in a container equipped with a reflux condenser. In the process of evolution of hydrogen gas, the mixture reacted violently. After the metallic aluminum in the mixture was dissolved, the reaction mixture was cooled, and small quantities of sediment were removed by filtration. As a result, 49 ml of a colorless, clear solution of basic aluminum chloride was obtained. The basicity degree of the substance was 0.75. When the same method was employed with greater amounts of granular metallic aluminum, the resulting basic aluminum chloride aqueous solutions had basicity degree of 0.80 and 0.83.

Case 1

Eighty milliliters (80 ml) of basic aluminum chloride (basicity=0.83, Al content: 10.6%, Cl content: 7.15%) was added to 820 ml of water. While vigorously agitating the mixture, 100 ml of sodium sucrose octasulfate solution (found to contain 21.4 g) was added. After stirring for 5 minutes at room temperature, the reaction solution was left undisturbed, and the supernatant was removed by decantation. Then, after adding water once again and agitating the solution, the solution was left undisturbed. After having repeated the process 3 times, the total volume of the mixture was adjusted by adding water in order to produce 45 ml of slurry. The slurry was then immediately wet-milled for 10 minutes in a bench-top colloid mill (Mill Mix: manufactured by Nihon Seiki Seisakujo), giving rise to 40 ml of sucralfate aqueous suspension stock (ULW-M). The concentration of the stock was 1.2 g/ml of sucralfate. When analyzed by a laser-diffraction equipment for particle size distribution measurement (manufactured by Nikkiso), the stock was found to contain particles of 50 µm or less, forming in 97.5% of all particles.

Case 2

Using basic aluminum chloride of different basicities (0.67, 0.80, and 0.83), sucralfate aqueous suspension stocks were produced as described in Reference Example 3. The number of washing cycles during production, after the reaction, for each sucralfate wet powder slurry was compared. The results are shown in Table 1.

TABLE 1

| Basicity | No. of Washing Cycles |
| --- | --- |
| 0.67 | 5 |
| 0.80 | 2–3 |
| 0.83 | 2–3 |

It was found that performing the micronizing process immediately after washing process was possible. Further, it became clear that as the basicity of basic aluminum chloride increased, the number of washing cycles could be decreased.

Case 3

After combining 513 g of sucralfate wet powder, produced in Reference Example 1, with 632 ml of water and dispersing the powder, the mixture was wet-milled for 20 minutes at an open angle of 30° and a speed of 5,000 rpm using a bench-top colloid mill (Mill Mix: manufactured by Nihon Seiki Seisakujo). After sampling at 5-minute intervals during milling, particle size distribution and time-sequential changes in sedimentation were measured with laser-diffraction equipment for particle size distribution measurement (produced by Nikkiso). This process resulted in about 1 liter of aqueous suspension stock for use in production of sucralfate preparations (ULW-M).

For purposes of comparison, unmilled, aqueous suspension stock (ULW) was prepared by simply shaking sucralfate wet powder in water, identical to the same sample of this case without milling process.

For further comparison with the conventional example, 328 g of spray-dried sucralfate dry powder without milling process was added to 823 ml of water and then thoroughly mixed to form about 1 liter of suspension (ULD).

Additionally, 337 g of milled sucralfate, produced by micronizing of spray-dried sucralfate dry powder with an impact pulverizer, was combined with 817 ml of water, followed by thorough mixing of the mixture, about 1 liter of suspension (ULD-M) was prepared.

Each sample was evaluated in a similar manner in terms of particle-size distribution and time-sequential changes in the sedimentation volume ratio (%).

The particle-size distribution results and the time-sequential changes in the sedimentation volume ratio appear in Tables 2 and 3, respectively.

TABLE 2

| Sample | Particle-Size Distribution | |
|---|---|---|
| | Below 50 μm (%) | Average (μm) |
| ULW | 74.6 | 43.7 |
| ULW-M | 97.7 | 13.7 |
| ULD | 82.2 | 27.5 |
| ULD-M | 100.0 | 8.0 |

TABLE 3

| | Sedimentation Volume Ratio | | | | | | | |
|---|---|---|---|---|---|---|---|---|
| | Sedimentation Volume Ratio (%) | | | | | | | |
| | Days Lapsed | | | | | | | |
| Sample | 0 | 1 | 2 | 4 | 6 | 10 | 19 | 31 | 48 |
| ULW | 100 | 64 | 62 | 62 | 62 | 62 | 61 | 61 | 61 |
| ULW-M | 100 | 83 | 71 | 70 | 70 | 70 | 68 | 68 | 68 |
| ULD | 100 | 98 | 83 | 85 | 84.5 | 84.5 | 84 | 83 | 82.5 |
| ULD-M | 100 | 98 | 86 | 82 | 81 | 80.5 | 79 | 79 | 78 |

Case 4

The sucralfate aqueous suspension stock of this invention (ULW-M), which was prepared in Case 3, and particles of the comparison samples (ULW, ULD, and ULD-M) were evaluated in terms of changes in particle size distribution.

After storing each sample for either 58 days at room temperature or 43 days under accelerated condition at 50° C., the average particle-size distribution particles below 50 Al were determined by laser-diffraction equipment for particle size distribution measurement (produced by Nikkiso).

The results appear in Table 4.

TABLE 4

| | Changes in Particle Size | | |
|---|---|---|---|
| Sample | Initial Avg. Particle Size (Al) Accum. (%) under 50 μm | After 58 days of storage at room temperature Avg. Particle Size (Al) Accum. (%) under 50 μm | After 43 days at 50° C. Avg. Particle Size (Al) Accum. (%) under 50 μm |
| ULW | 43.7 | 41.8 | 38.0 |
| | 74.6 | 78.9 | 74.7 |
| ULD | 27.5 | 25.4 | 24.2 |
| | 82.2 | 84.5 | 86.5 |
| ULW-M | 13.7 | 13.7 | 13.1 |
| | 97.7 | 97.7 | 98.2 |
| ULD-M | 8.0 | 7.8 | 7.8 |
| | 100.0 | 100.0 | 100.0 |

Case 5

After storing the sucralfate aqueous suspension stock of this invention for 58 days, the agglutinability of the stock under an acidic condition through addition of hydrochloric acid was investigated.

After storing the sucralfate aqueous suspension stock of this invention (ULW-M), which was prepared in Case 3, and conventionally prepared sucralfate (ULD-M) for 58 days at room temperature, 6 ml of 0.1N hydrochloric acid was added to 1 g samples of both stocks (each equivalent to 200 mg of sucralfate). The samples were then observed with the naked eye for agglutination during shaking, and the time required for agglutination was measured. The judgment as to whether or not each mixture had agglutinated was made after 30 minutes.

The results appear in Table 5. They represent the average measurements of three trials.

TABLE 5

| Sample (Stored at room temp. for 58 days) | Time to agglutination (seconds) | Observation after 30 min |
|---|---|---|
| ULW-M | 264 | Agglutinated |
| ULD-M | — | Not agglutinated |

Case 6

After adding 383 g of wet sucralfate powder to 797 ml of water and dispersing the powder, the mixture was wet-milled with a bench-top colloid mill (Mill Mix: produced by Nihon Seiki SeisakuJo). About 1 liter of aqueous suspension stock for use in production of sucralfate preparations was thus obtained. While milling, sampling was performed at 5-minute intervals, and average particle size, particle size at the 50% accumulation level, and the percentage of particles below 50% μm were investigated using laser-diffraction equipment for particle size distribution measurement (produced by Nikkiso). The results appear in Table 6.

TABLE 6

| Milling Time (Min) | Average Particle (μm) | Particle Size at 50% Accumulation Level (μm) | Particles below 50 μm Percentage (%) |
|---|---|---|---|
| 0 | 30.1 | 22.3 | 81.2 |
| 5 | 14.9 | 10.1 | 96.5 |

TABLE 6-continued

| Milling Time (Min) | Average Particle (μm) | Particle Size at 50% Accumulation Level (μm) | Particles below 50 μm Percentage (%) |
|---|---|---|---|
| 10 | 12.9 | 8.7 | 98.5 |
| 15 | 12.1 | 8.0 | 99.0 |

From Table 6, it is clear that after about 5 minutes, the distribution of particles below 50 μm was greater than 98% and after about 10 minutes both average particle size and particle size at the 50% accumulation level had reached to almost invaluable degree.

Case 7

The sedimentation characteristics of aqueous suspension made of sucralfate dry powder obtained from Reference Example 2 (ULD-M) and aqueous suspension made of sucralfate wet powder obtained from Case 6 (ULW-M) were investigated.

Two, 100 ml samples of each aqueous suspension stock were infused into separate 100 ml mess cylinders and allowed to stand at either room temperature or 50° C. The sucralfates sedimented, all separating into an upper layer of water and a lower layer of sucralfate slurry. The ratio of the slurry layer to the whole varied according to the type of suspension and the temperature, but after about one week all suspensions reached to nearly invaluable value. The ratio of the volume of slurry to the whole after one and two weeks, in addition to the density of the sedimented slurry portion after 2 weeks (average density), was measured. The results appear in Table 7.

TABLE 7

| | Volume of the sedimented slurry layer | | Density of the sedimented slurry |
|---|---|---|---|
| | After 1 week | After 2 weeks | |
| ULW-M | 64% | 63% | 1.18 g/ml |
| | (59%) | (59%) | (1.19 g/ml) |
| ULD-M | 62% | 62% | 1.16 g/ml |
| | (55%) | (55%) | (1.20 g/ml) |

Note:
The values inside the parentheses represent values obtained from samples allowed to stand at 50° C.

The two suspension slurries had equal densities of approximately 1.2 g/ml, indicating the existence of a critical slurry density at which the water layer does not separate further. This critical slurry concentration depends on the particle size of the sucralfate, and even if the particle size is reduced, the concentration may be lowered so that the water layer does not separate further. As shown in Table 7, the aqueous suspension obtained from this invention has a particle size set no higher than 50 μm, and if the sucralfate concentration is set no lower than 1.2 g/ml, a uniform sucralfate suspension which is difficult to separate into two layers, water and slurry layers, can be manufactured.

Case 8

The stability of two suspensions prepared in accordance with Case 7 was investigated.

Each suspensions (at room temperature and 50° C.) was sampled periodically and at every sampling the equivalent of about 1 g of wet powder obtained by filtration was dissolved in 10 ml of the mixture of sulfuric acid and sodium hydroxide. After adding 15 ml of 0.1N sodium hydroxide to each sample, affording a clear solution, 50 μl of each solution was analyzed by high performance liquid chromatography (HPLC). The results appear in Table 8.

TABLE 8

| | Peak Area Ratio of Octasulfate (%) | | |
|---|---|---|---|
| | After 5 Days | After 6 Days | After 13 Days |
| ULW-M | 98.1 | 98.3 | 98.4 |
| | (1.9) | (1.7) | (1.6) |
| | 97.7 | 97.0 | 98.3 |
| | (2.3) | (3.0) | (1.7) |
| ULD-M | 97.0 | 95.8 | 97.0 |
| | (3.0) | (4.2) | (3.0) |
| | 97.5 | 96.3 | 96.6 |
| | (2.5) | (3.7) | (3.4) |

Note:
For each sample, the upper values represent the values obtained with samples stored at room temperature and the lower values represent the values obtained with samples stored at 50° C. The values inside the parentheses represent the HPLC peak area ratio of heptasulfate (%).

There was not found to be a periodical change in the ratio of octasulfate or the heptasulfate between both suspensions.

Since a little decomposition of ULD-M into heptasulfate ester is formed to be occurred in the heat-drying process of wet sucralfate powder, ULW-M is superior in terms of stability.

Case 9

Using two suspensions identical to those in Cases 7 and 8, the acid-neutralizing behavior of each was investigated. By dispersing each suspension equivalent to 150 mg of sucralfate in 80 ml of distilled water at room temperature, followed by very slowly adding dropwise 0.1N hydrochloric acid under stirring, change to a glutinous state with pH change were observed with the naked eye, recording addition volume. The results appear in Table 9.

TABLE 9

| | Addition volume and pH at the time of change of suspension condition of glutinous state | Addition volume per sucralfate |
|---|---|---|
| ULW-M | 4.5 ml pH 2.7 | 0.029 ml |
| ULD-M | 6.2 ml pH 3.2 | 0.044 ml |

As shown in Table 9, suspension obtained from this invention changes into a viscous substance (glutinous state) at a lower addition volume than does conventional ULD-M.

Test Example 1

The in vitro activities (protein absorptivity and antipepsin activity) of sucralfate aqueous suspension stock prepared from the wet powder of this invention (ULW-M) and suspension stock prepared from conventional dry powder (ULD-M) were compared.

(Protein absorptivity)

About six gram of bovine serum albumin (BSA) was measured out precisely, and dissolved in a Clark-Larks buffer solution (CLB) to make a BSA reference stock solution of precisely 1000 ml. The sucralfate aqueous suspension stock of this invention (ULW-M) and the conventional sucralfate aqueous suspension stock produced from finely milled dry powder (ULD-M) were sampled in quantities ranging from 0.15 g to 3.0 g, and each sample was added to 50 ml of BSA reference stock solution, respectively.

The mixtures were incubated at 37° C. for 80 minutes, and immediately after incubation the mixtures were adjusted to precisely 200 ml using CLB. The mixtures were then filtered to make the test solutions.

Separately, diluting the BSA reference stock solution, BSA reference standard solutions of 0.1, 0.2, 0.4, 0.6, 0.8, and 1.0 mg/ml were prepared, respectively.

Five (5) ml of a protein assay reagent (produced by Bio-Rad) was added to 0.1 ml of each of the reference standard solutions and test solutions.

The absorbance at 595 nm of wavelength was measured. Using the calibration curve of the reference solutions, the quantity of non-absorbed BSA in each test solution was determined. Absorption curves were drawn by comparing the ratio of the sucrose octasulfate (SOS) to the BSA on the X-axis and non-absorbed BSA on the Y-axis.

The results appear in FIG. 1.

As clearly shown in FIG. 1, there was essentially no difference in protein absorption activity found between the product of this invention (ULW-M) and the conventional product (ULW-D).

(Antipepsin Activity)

Three 0.5 ml of sucralfate suspensions (final concentrations: 0, 10, and 50 mg/ml, respectively) were each combined with a 2.5 ml solution consisting of pepsin dissolved in Clark-Larks buffer solution (100 μg/ml) and incubated for 20 minutes at 37° C.

The mixtures were then placed in a centrifuge (3000 rpm, 5 minutes), thus removing the insoluble substance.

Taking two 0.5 ml samples from each supernatant, the rate of sucralfate-bound protein and antipepsin activity rate were determined, respectively.

Figure 4:
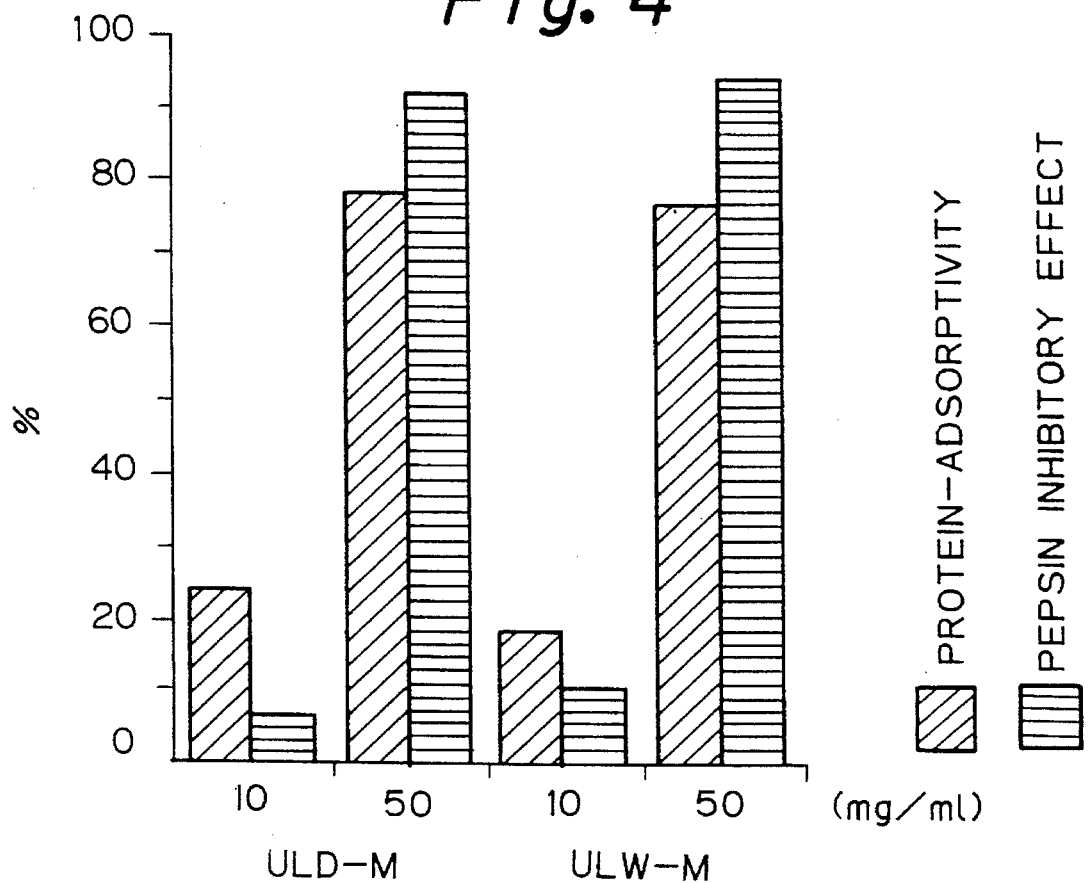
FIG. 4 is a graph comparing ULW-M and ULD-M in terms of protein absorptivity and pepsin inhibitory effect.

The results appear in FIG. 4. There was almost no difference between the sucralfate suspension of this invention (ULW-M) and the conventional suspension (ULD-M).

Test Example 2

The in vivo pharmacological activities of sucralfate aqueous suspension stock prepared from the wet powder of this invention (ULW-M) and suspension stock prepared from conventional dry powder (ULW-D) were studied and compared.

By creating a Shay ulcer model and an ethanol-induced acute gastric mucosal disorder model using groups of ten, seven-week old SD rats, the pharmacological efficacy of sucralfate was investigated.

(Shay ulcer model)

After depriving the rats of all food for 48 hours, abdominal sections were performed and the pylori ligated with the animals under ether anesthesia. A liquid preparation of sucralfate suspension was then administered orally in a dosage of 1 ml/kg. Then, after depriving the animals of water for a further 18 hours, the rats were sacrificed, the stomachs removed, and the antiulcerant effects of the sucralfate were evaluated. The evaluation was performed on a scale (score) from 0–5 in accordance with the Adami's method.

(Ethanol-induced acute gastric mucosal disorder model)

A liquid preparation of sucralfate suspension was administered in the dosage of 1 ml/kg orally to rats which had been deprived of good for the preceding 24 hours and water for the preceding 18 hours. One hour after sucralfate administration, ethanol was administered, and then two hours following the second administration the rats were sacrificed and the stomachs removed. The evaluation was expressed in terms of the sum of the longest distance (mm) across the injured gastric mucosal areas.

Figure 2:
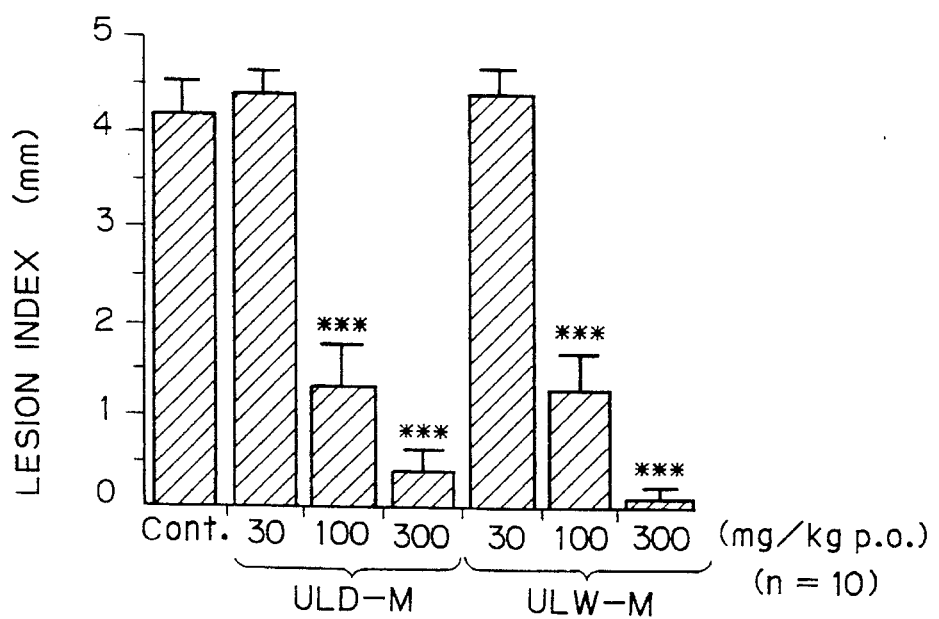
FIG. 2 is a graph showing the in vivo inhibitory effects of ULW-M and ULD-M in Shay ulcer in rat.

Results (1) The suppressive activity against Shay ulcer is shown in FIG. 2. When comparing samples of both ULW-M and ULD-M administered in doses above 100 mg/kg both suspensions showed significant suppressive activity to a control (vehicle). There was no significant difference found between the activities of the ULW-M and the ULD-M.

Figure 3:
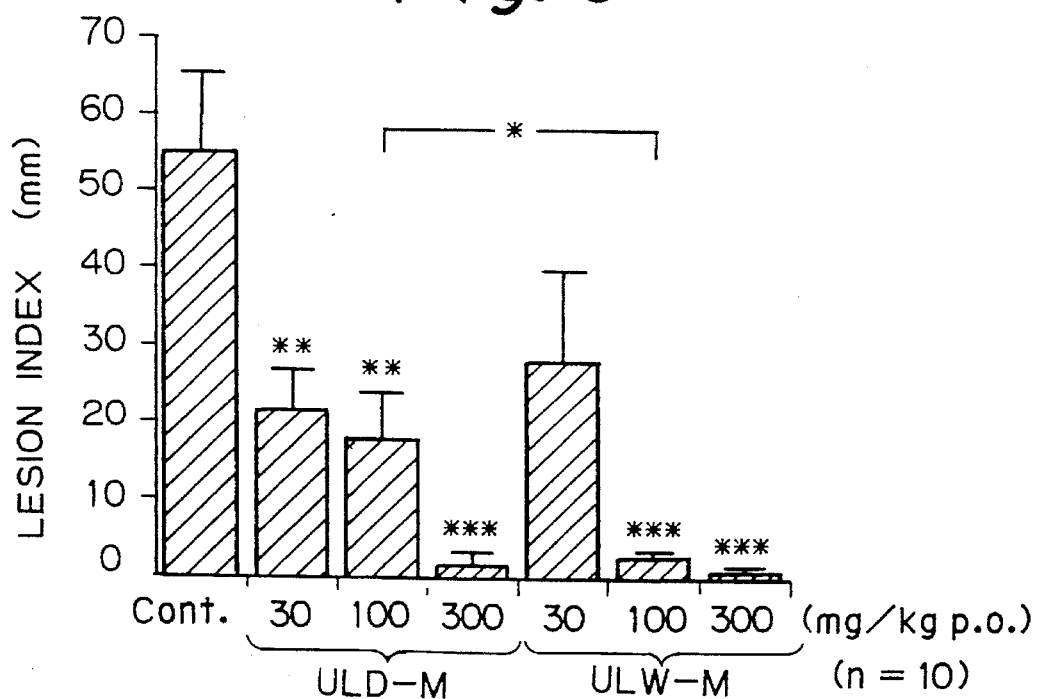
FIG. 3 is a graph showing the in vivo inhibitory effects of ULD-M and ULW-M in ethanol-induced acute gastric mucosal lesion.

(2) The results of suppressive activity against ethanol-induced acute gastric mucosal disorder is shown in FIG. 3. No significant difference between ULW-M and ULD-M was found.

Test Case 2

Characteristics of preparations

Using the preparation manufactured in followed Production Example 5 (ULW-C) and the sucralfate suspension stock of this invention (ULW-M) as a reference, tests were performed concerning protein absorption activity, as described in Test Case 1, and suppressive activity against ethanol-induced gastric mucosal disorder, as described in Test Case 2.

Figure 5:
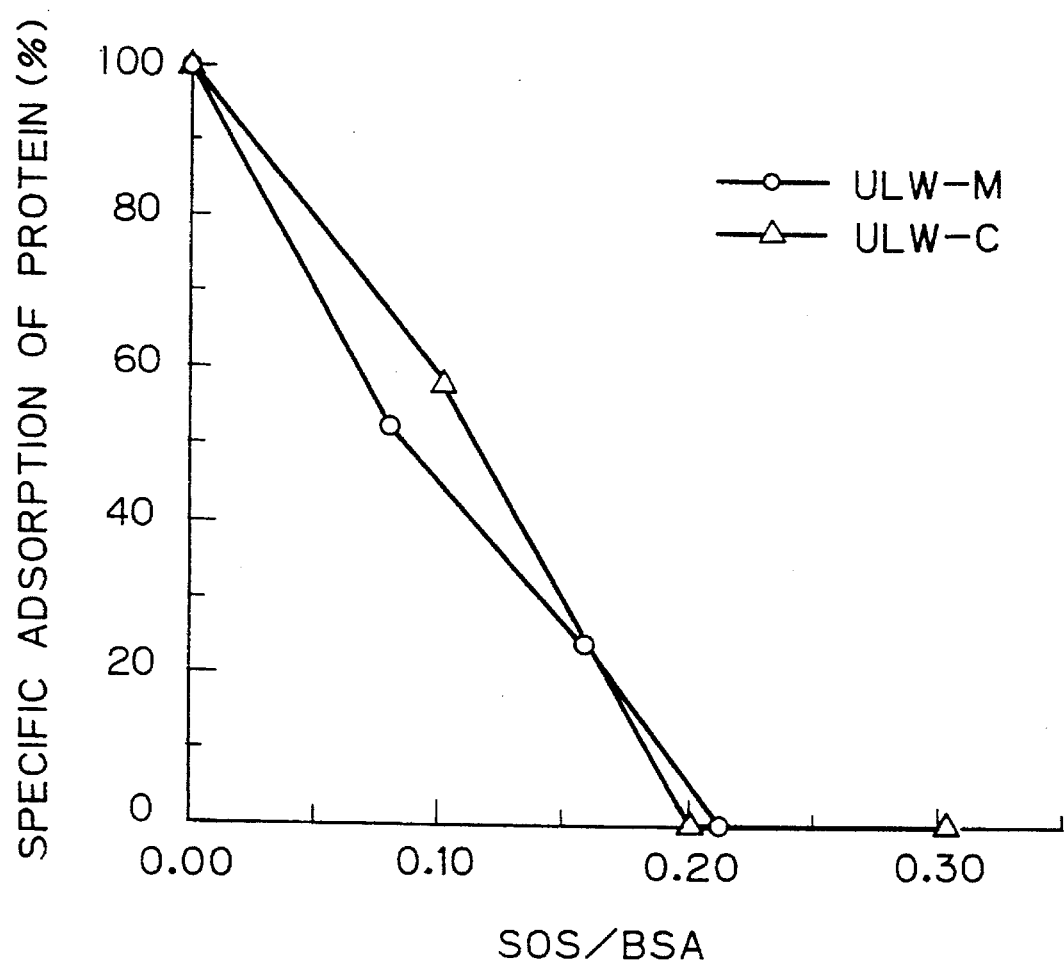
FIG. 5 is a graph showing a comparison of protein absorptivities in suspension preparations produced from sucralfate aqueous suspension stock (ULW-M). ULW-C represents preparations which were produced from ULW-M using production example 5.
Figure 6:
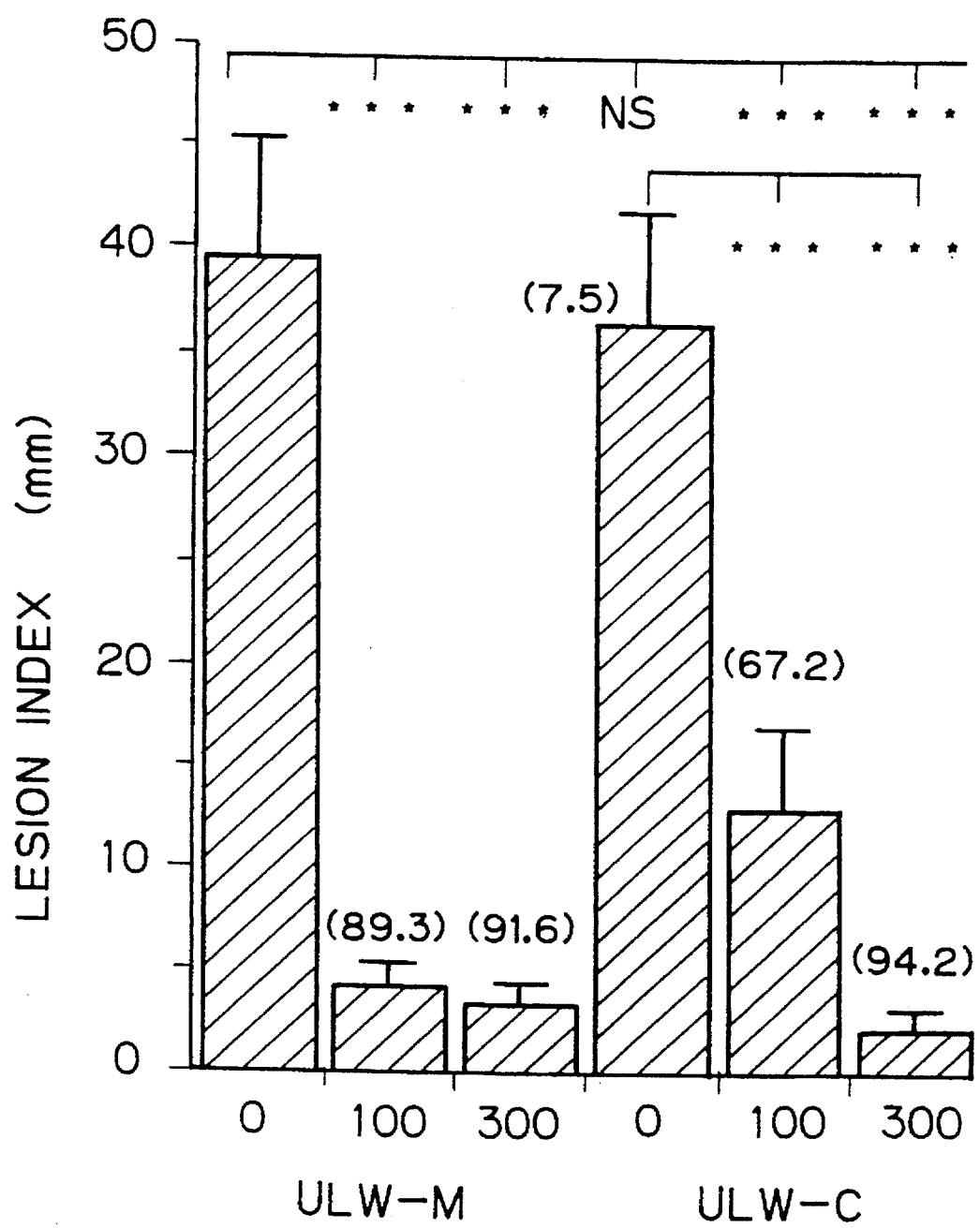
FIG. 6 is a graph comparing the in vivo inhibitory effects of ULW-M and ULW-C samples on ethanol-induced acute gastric mucosal lesion.

The results of the two tests are summarized in FIGS. 5 and 6, respectively.

Results

In vitro and in vivo activities of ULW-M were found to be unchanged when measured in preparations using ULW-M.

Production Example 1

| Ingredients | Content |
| --- | --- |
| Sucralfate, aqueous suspension stock | Equivalent to 100.0 g |
| 85% Glycerin | 100.0 g |
| Xanthan Gum | 2.5 g |
| Sodium phosphate dihydrogen | 2.5 g |
| Purified Water, a sufficient quantity to make | 500 ml |

The above-listed ingredients were combined to produce a preparation of sucralfate aqueous suspension. The suspension had a pH of 4.91, a specific gravity of 1.16, and a viscosity of 291.7 cps. The preparation was found to be of excellent quality in terms of dispersal and adhesive characteristics.

Production Example 2

| Ingredients | Content |
| --- | --- |
| Sucralfate, aqueous suspension stock | Equivalent to 50.0 g |
| HPS* | 15.0 g |
| Purified Water, a sufficient quantity to make | 500 ml |
| HPS: Hydroxypropyl Starch | |

The above-listed ingredients were combined to obtain a preparation of sucralfate aqueous suspension. The suspension had a pH of 4.21, a specific gravity of 1.06, and a viscosity of 53.4 cps. The preparation was found to be of excellent quality in terms of dispersal and adhesive characteristics.

Production Example 3

| Ingredients | Content |
| --- | --- |
| Sucralfate, aqueous suspension stock | Equivalent to 50.0 g |
| 85% Glycerin | 100.0 g |

-continued

| Ingredients | Content |
| --- | --- |
| HPS | 15.0 g |
| Sodium phosphate dihydrogen | 2.5 g |
| Purified Water, a sufficient quantity, to make | 500 ml |

The above-listed ingredients were combined to obtain a preparation of sucralfate aqueous suspension. The suspension had a pH of 4.90, a specific gravity of 1.09, and a viscosity of 44.2 cps. The preparation was found to be of excellent quality in terms of dispersal and adhesive characteristics.

Production Example 4

| Ingredients | Content |
| --- | --- |
| Sucralfate, aqueous suspension stock | Equivalent to 100.0 g |
| 85% Glycerin | 100.0 g |
| HPS | 12.5 g |
| Sodium phosphate dihydrogen | 2.5 g |
| Purified Water, a sufficient quantity, to make | 500 ml |

The above-listed ingredients were combined to obtain a preparation of sucralfate aqueous suspension. The suspension had a pH of 4.93, a specific gravity of 1.10, and a viscosity of 40.6 cps. The preparation was found to be of excellent quality in terms of dispersal and adhesive characteristics.

Production Example 5

| Ingredients | Content |
| --- | --- |
| Sucralfate, aqueous suspension stock | Equivalent to 100.0 g |
| 85% Glycerin | 100.0 g |
| HPS | 15.0 g |
| Sodium phosphate dihydrogen | 2.5 g |
| Purified Water, a sufficient quantity, to make | 500 ml |

The above-listed ingredients were combined to obtain a preparation of sucralfate aqueous suspension (preparation solution for administration). The preparation was found to be of excellent quality in terms of dispersal and adhesive characteristics.

Effect of Invention

The preceding data, comparing this invention's sucralfate aqueous suspension stock obtained directly from wet powder with the conventional stock obtained from dry powder, showed equivalency between the two stocks in terms of properties and pharmacological activities. Accordingly, in solving the problems existing in the conventional production method, we were able to obtain an sucralfate aqueous suspension stock having both the same properties and pharmacological activities as the original substance. In other words, without using the operationally defective processes of 1 heat drying—2 milling—3 suspending in water, this invention enables us to obtain bulk material at low cost and with a shortened process. Furthermore, free from the problem of escaping micronized particles which arise in the milling of dry powder, wet-powder milling in water is a technologically superior process which does not pollute the working environment (preventing health of workers). Additionally, wet-milling provides for simpler adjustment of particle size than does dry-milling and for possible arrangement of continuous production process. Also, since there is no spreading of micronized powder during shipment or in the production stage of preparations, environmental pollution arising from the preparation process can be prevented.

We claim:

1. A process for producing an aqueous sucralfate suspended stock solution which comprises reacting sodium sucrose sulfate with a basic aluminum chloride having a basicity degree of from 0.67 to 0.75, dispersing the resulting sucralfate particles in water and milling the particles to an average particle size of less than 50 μm without drying the particles.

2. A process according to claim 1 wherein the resulting sucralfate particles in an aqueous medium are milled without performing either solid-liquid separation or drying.

3. A process according to claim 1 wherein said dispersing of sucralfate particles provides a concentration of 1–2 g/ml of said sucralfate.

4. a process according to claim 1 wherein the basic aluminum chloride has a bascity degree of 0.67 or 0.75.

5. A process according to claim 4, wherein the basic aluminum chloride has a basicity degree of 0.67.

6. A process according to claim 1 wherein said basic aluminum chloride comprises aluminum dihydroxy chloride.

* * * * *